US012427314B2

(12) United States Patent
Kent (10) Patent No.: US 12,427,314 B2
(45) Date of Patent: Sep. 30, 2025

(54) NEUROMODULATION OF THE GLOSSOPHARYNGEAL NERVE TO IMPROVE SLEEP DISORDERED BREATHING

(71) Applicant: Vanderbilt University, Nashville, TN (US)

(72) Inventor: David T. Kent, Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 409 days.

(21) Appl. No.: 17/642,850

(22) PCT Filed: Sep. 11, 2020

(86) PCT No.: PCT/US2020/050335
§ 371 (c)(1),
(2) Date: Mar. 14, 2022

(87) PCT Pub. No.: WO2021/050829
PCT Pub. Date: Mar. 18, 2021

(65) Prior Publication Data
US 2022/0379114 A1  Dec. 1, 2022

Related U.S. Application Data

(60) Provisional application No. 62/961,338, filed on Jan. 15, 2020, provisional application No. 62/900,442, filed on Sep. 13, 2019.

(51) Int. Cl.
*A61N 1/36* (2006.01)
*A61N 1/05* (2006.01)

(52) U.S. Cl.
CPC ........ *A61N 1/3611* (2013.01); *A61N 1/36139* (2013.01); *A61N 1/36175* (2013.01); *A61N 1/0551* (2013.01)

(58) Field of Classification Search
None
See application file for complete search history.

(56) References Cited

U.S. PATENT DOCUMENTS

2001/0018547 A1* 8/2001 Mechlenburg ......... A61N 2/006
600/15
2006/0293723 A1* 12/2006 Whitehurst ........ A61N 1/36071
607/48
(Continued)

OTHER PUBLICATIONS

Vaskovic J. (Nov. 23, 2023). Glossopharyngeal nerve (cranial nerve IX). Kenhub. https://www.kenhub.com/en/library/anatomy/the-glossopharyngeal-nerve (Year: 2023).*
(Continued)

*Primary Examiner* — Benjamin J Klein
*Assistant Examiner* — Willow Grace Welch
(74) *Attorney, Agent, or Firm* — Tarolli, Sundheim, Covell &Tummino LLP (57) ABSTRACT

Methods and systems are provided to improve SDB in a patient suffering therefrom by delivering an electrical neuromodulation signal to at least a target site comprising an efferent fiber of the glossopharyngeal nerve that innervates pharyngeal constrictor muscles or the stylopharyngeus muscle. Methods include further delivering electrical neuromodulation signals to other sites including one or more combinations of the ansa cervicalis, the hypoglossal nerve, the palatoglossus muscle, and/or the palatopharyngeus muscle. The electrical neuromodulation signal delivered to efferent fibers of the glossopharyngeal nerve can be done independent of a detected sensory or input signal that measures the neuromuscular state of the patient's airway.

14 Claims, 7 Drawing Sheets (56) References Cited

U.S. PATENT DOCUMENTS

| | | | |
|---|---|---|---|
| 2007/0027482 A1* | 2/2007 | Parnis | A61N 1/0551 607/2 |
| 2007/0027483 A1* | 2/2007 | Maschino | A61N 1/36053 607/2 |
| 2011/0093032 A1 | 4/2011 | Boggs, II | |
| 2011/0230702 A1 | 9/2011 | Honour | |
| 2012/0150255 A1 | 6/2012 | Lindenthaler | |
| 2014/0228905 A1* | 8/2014 | Bolea | A61F 5/56 607/42 |
| 2018/0117316 A1 | 5/2018 | Wagner et al. | |

OTHER PUBLICATIONS

International Search Report and Written Opinion mailed Jan. 27, 2021 for corresponding International Application No. PCT/US2020/050335.

Extended European Search Report (EESR) for corresponding EP Application No. 20863143, dated Jul. 31, 2023, pp. 1-7.

* cited by examiner

Delivering a first electrical neuromodulation signal to a target site comprising efferent fibers of the glossopharyngeal nerve that innervates one or more pharyngeal constrictor muscles and/or a stylopharyngeus muscle
202

Delivering a second electrical neuromodulation signal to a target site comprising an ansa cervicalis
204

Improving the patient's SDB via delivery of the first and second electrical neuromodulation signals
206

NEUROMODULATION OF THE GLOSSOPHARYNGEAL NERVE TO IMPROVE SLEEP DISORDERED BREATHING

CROSS-REFERENCE TO RELATED APPLICATIONS

The present application is a U.S. National Stage application under 35 USC 371 of PCT Application Serial No. PCT/US2020/050335, filed on 11 Sep. 2020, which claims priority to U.S. Provisional Patent Application No. 62/900,442 filed on Sep. 13, 2019 and U.S. Provisional Application No. 62/961,338 filed on Jan. 15, 2020. The contents of each are incorporated by reference in their entirety.

TECHNICAL FIELD

The present disclosure relates to methods and systems for treating sleep disordered breathing by neuromodulating an efferent fiber of the glossopharyngeal nerve.

BACKGROUND

Sleep disordered breathing (SDB) occurs when there is a partial or complete cessation of breathing that occurs many times throughout the night. Obstructive sleep apnea (OSA) is a type of SDB that involves cessation or significant decrease in airflow in the presence of breathing effort. It is the most common type of SDB and is characterized by recurrent episodes of upper airway collapse during sleep inducing repetitive pauses in breathing followed by reductions in blood oxygen saturation or neurologic arousal. The pathophysiology of OSA can involve factors such as craniofacial anatomy, airway collapsibility, and neuromuscular control of the upper airway dilator musculature. Electromyogram studies have shown that the tonic and phasic activity of the pharyngeal airway dilatory muscles (such as the genioglossus muscle) progressively reduced from wakefulness to non-rapid eye movement sleep to rapid eye movement sleep.

Continuous positive airway pressure (CPAP) therapy is the frontline treatment for OSA. CPAP therapy utilizes machines, generally including a flow generator, tubing, and a mask designed to deliver a constant flow of air pressure to keep the airways continuously open in patients with OSA. However, the success of CPAP therapy is limited by compliance with reported rates ranging from 50% to 70%. Hypoglossal nerve stimulation (HNS) has now been established as an effective form of therapy for patients with obstructive sleep apnea (OSA) who are unable to tolerate positive airway pressure. This therapy works by protruding and stiffening the tongue muscle thereby dilating the pharyngeal airway. However, only a small subset of patients with OSA have anatomy suitable for hypoglossal nerve stimulation therapy, as many patients continue to suffer from airway collapse even with stimulation of tongue musculature.

SUMMARY

Providing herein are methods and systems to improve SDB by neuromodulating an efferent fiber of the glossopharyngeal nerve (cranial nerve IX). In certain aspects, a method to improve sleep disordered breathing in a patient suffering therefrom comprises delivering an electrical neuromodulation signal to a target site comprising an efferent fiber of the glossopharyngeal nerve that innervates one or more pharyngeal constrictor muscles or a stylopharyngeus muscle independent of a detected or sensed sensory or input signal regarding the neuromuscular state of the patient's airway. The method further comprises improving the patient's SDB via delivery of the electrical neuromodulation signal.

In certain aspects, methods and systems are provided herein to improve SDB in a patient suffering therefrom by delivering electrical neuromodulation signals to multiple airway sites. Such airway sites can include one more combinations of an efferent fiber of the glossopharyngeal nerve (cranial nerve IX); the ansa cervicalis; the hypoglossal nerve (HGN); the palatoglossus muscle; or the palatopharyngeus muscle. For example, a method can include delivering electrical neuromodulation signals to one or more combinations of a target site comprising an efferent fiber of the glossopharyngeal nerve that innervates one or more pharyngeal constrictor muscles that when activated, increases pharyngeal muscle tone or that innervates a stylopharyngeus muscle that, when activated, moves the pharyngeal wall laterally; a target site comprising an ansa cervicalis that innervates one or more infrahyoid muscles that, when activated, pulls down on the airway creating caudal tension or traction and reducing pharyngeal wall collapse; a target site comprising the hypoglossal nerve (HGN) that innervates one or more muscles that, when activated, tenses the tongue musculature to reduce tongue-related airway obstruction; a target site comprising the palatoglossus muscle or an innervating nerve fiber thereof that, when activate, depresses and pulls the soft palate anteriorly and inferiorly to dilate and open the retropalatal airspace of the patient; or a target site comprising the palatopharyngeus muscle or an innervating nerve fiber thereof that, when activated, pulls the soft palate inferiorly to dilate and open the retropalatal airspace of the patient. The method can further include improving the patient's SDB via delivery of the electrical neuromodulation signals.

In certain aspects, a method to improve SDB in a patient suffering therefrom comprises delivering a first electrical neuromodulation signal to a target site comprising an efferent fiber of the glossopharyngeal nerve that innervates one or more pharyngeal constrictor muscles that, when activated, increases pharyngeal muscle tone or a stylopharyngeus muscle that, when activated, moves the pharyngeal wall laterally. The method further includes delivering a second electrical neuromodulation signal to a target site comprising an ansa cervicalis that innervates one or more infrahyoid muscles that, when activated, pulls down on the airway creating caudal tension or traction and reducing pharyngeal wall collapse. The method further comprises improving the patient's SDB via delivery of the first and second electrical neuromodulation signals.

DETAILED DESCRIPTION

Provided herein are methods and systems to improve SDB in a patient suffering therefrom by delivering an electrical neuromodulation signal to at least a target site comprising an efferent fiber of the glossopharyngeal nerve (cranial nerve IX) that innervates pharyngeal constrictor muscles or a stylopharyngeus muscle. Non-limiting examples of SDBs are increased upper airway resistance including snoring; upper airway resistance syndrome (UARS); and sleep apnea. Sleep apnea can include OSA, central sleep apnea (CSA), and complex sleep apnea. As used herein with respect to a described element, the terms "a," "an," and "the" include at least one or more of the described element(s) unless otherwise indicated. Further, the terms "or" and "and" refer to "and/or" and combinations thereof unless otherwise indicated. The terms "first," "second," etc. are used to distinguish one element from another and not used in a quantitative sense unless indicated otherwise. Thus, a "first" element described below could also be termed a "second" element. Reference to "improving" a patient's SDB includes reducing the symptoms of, mitigating, or preventing the SDB. In certain aspects, a method of improving a patient's SDB is preventative as opposed to reactionary in nature. In other words, a method of improving a patient's SDB according to certain aspects involves preventing SDB as opposed to detecting an apnea or hypopnea event, for example, and responding to such detected event. By preventing SDB, a treatment method can reduce the potential for airway collapse as opposed to reacting to a documented event. As used herein, "neuromodulation," "neuromodulate," "neurostimulation," "neurostimulate," "stimulation" or "stimulate" refers to exciting or inhibiting neural activity. Stimulation of sites described herein includes bilateral stimulation or unilateral stimulation. A patient suffering from SDB includes a mammal, such as a human being.

Figure 1:
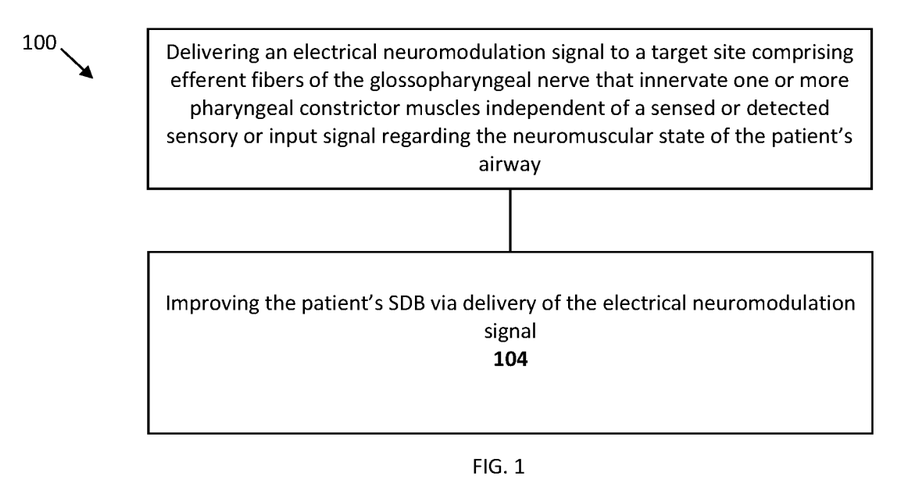
FIG. 1 is a flow chart depicting exemplary steps of a method to improve SDB in a patient suffering therefrom according to an aspect of the present disclosure.
Figure 2:
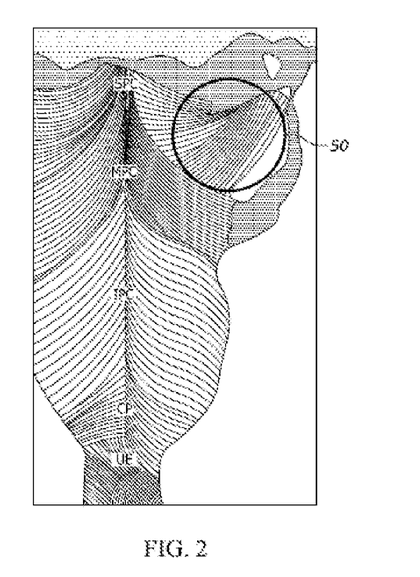
FIG. 2 is a schematic posterior view of the pharynx.

In an aspect and with reference to FIGS. 1 and 2, a method 100 to improve SBD in a patient suffering therefrom comprises delivering an electrical neuromodulation signal to a target site comprising an efferent fiber of the glossopharyngeal nerve that innervates one or more pharyngeal constrictor muscles or a stylopharyngeus muscle 102. An exemplary target site 50 is identified in FIG. 2. When activated, such one or more pharyngeal constrictor muscles can increase pharyngeal muscle tone to reduce pharyngeal airway collapsibility. When activated, a stylopharyngeus muscle can move the pharyngeal wall laterally. In certain embodiments, an electrical neuromodulation signal is not delivered to sensory fibers that innervate the mucosal layers of the pharynx wall. Further, in certain embodiments, an electrical neuromodulation signal is delivered independent of sensory or input signals detected or sensed regarding the neuromuscular state of the airway. For example, an electrical neuromodulation signal can be delivered on a tonic basis or on a duty cycle independent of sensory or input signals detected or sensed regarding the neuromuscular state of the airway. In other words, even though sensory or input signals regarding the neuromuscular state of the airway can be measured, such sensory information may not dictate the stimulation parameters of the electrical neuromodulation signal delivered to the target site in certain embodiments. Method 100 further comprises improving the patient's SDB via delivery of the electrical neuromodulation signal 104. The target site can be the pharyngeal plexus.

In another aspect, methods and systems are provided to improve SDB in a patient suffering therefrom by delivering electrical neuromodulation signals to multiple airway sites. Such multiple airway sites can include one or more combinations of an efferent fiber of the glossopharyngeal nerve (cranial nerve IX) that innervates one or more pharyngeal constrictor muscles or the stylopharyngeus muscle; the ansa cervicalis; the hypoglossal nerve (HGN); the palatoglossus muscle or an innervating nerve fiber thereof; or the palatopharyngeus muscle or an innervating nerve fiber thereof. Methods can improve SDB by stimulating nerves and/or muscles to modulate genioglossus tone, caudal traction of the pharynx, and intrinsic muscle tone to improve pharyngeal airway patency. For example, methods to improve SDB can involve modulating intrinsic pharyngeal wall tone by stimulating an efferent fiber of the glossopharyngeal nerve, providing caudal traction to the upper airway by stimulating the ansa cervicalis, modulating genioglossus tone by stimulating the HGN, and/or combinations thereof. Methods can additionally or alternatively include stimulating the palatoglossus muscle or an innervating nerve fiber thereof to depress and pull the soft palate anteriorly and inferiorly to dilate and open the retropalatal airspace. Alternatively or in addition, methods can include stimulating the palatopharyngeus muscle or an innervating nerve fiber thereof to pull the soft palate inferiorly to dilate and open the retropalatal airspace of the patient.

Figure 3:
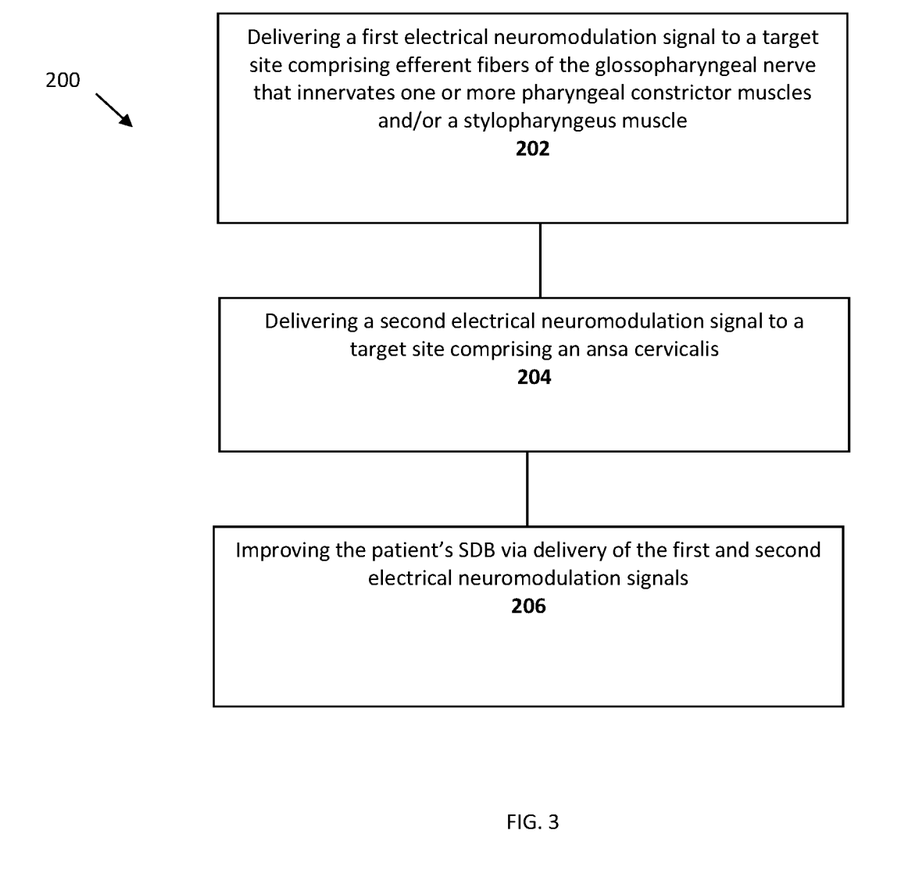
FIG. 3 is a flow chart depicting exemplary steps of a method to improve SDB in a patient suffering therefrom according to another aspect of the present disclosure.

Referring to FIG. 3, a method 200 to improve sleep disordered breathing (SDB) in a patient suffering therefrom comprises delivering a first electrical neuromodulation signal to a target site comprising an efferent fiber of the glossopharyngeal nerve that innervates one or more pharyngeal constrictor muscles or a stylopharyngeus muscle. When activated, an efferent fiber of the glossopharyngeal nerve that innervates one or more pharyngeal constrictor muscles can increase pharyngeal muscle tone. When activated, an efferent fiber of the glossopharyngeal nerve that innervates a stylopharyngeus muscle can move the pharyngeal wall laterally 202. The target site can comprise the pharyngeal plexus, for example. Method 200 can further include delivering a second electrical neuromodulation signal to a target site comprising an ansa cervicalis. When activated, a target site comprising an ansa cervicalis that innervates one or more infrahyoid muscles can pull down on the airway creating caudal tension or traction of the pharynx and reducing pharyngeal wall collapse 204. Method 200 further comprises improving the patient's SDB via delivery of the first and second electrical neuromodulation signals 206.

In another aspect, a method includes delivering an electrical neuromodulation signal to target site comprising an ansa cervicalis and further delivering an electrical neuromodulation signal to an efferent fiber of the glossopharyngeal nerve that innervates one or more pharyngeal constrictor muscles or the stylopharyngeus muscle; the hypoglossal nerve (HGN); the palatoglossus muscle or an innervating nerve fiber thereof; or the palatopharyngeus muscle or an innervating nerve fiber thereof.

Regarding delivering an electrical neuromodulation signal to a target site comprising an efferent fiber of the glossopharyngeal nerve in aspects referenced above, the side walls of the pharynx are constructed from the pharyngeal constrictors, which are innervated by the pharyngeal plexus that include fibers from cranial nerves IX and X. The nerves that innervate these muscles form a plexus over the outside surface of the pharyngeal constrictor muscles and then penetrate the pharyngeal constrictor muscles to reach the palatoglossus and palatopharyngeus muscles. Research suggests the motor branches of cranial nerve IX may be responsible for respiratory control of the constrictor muscles and that they can be identified in the region of the stylopharyngeus muscle. Increased constrictor muscle tone during respiration can reduce pharyngeal collapsibility by stiffening the pharyngeal walls. Stiffening of the pharyngeal walls without complete constriction may render stimulation of the ansa cervicalis and hypoglossal nerve more effective. Stimulation of the stylopharyngeus muscle may increase airway caliber by moving the pharyngeal wall laterally, and may also counterbalance a pharyngeal narrowing component of constrictor muscle activation that may occur if muscle activation advances beyond initial pharyngeal wall stiffening. In certain embodiments, an electrical neuromodulation signal is delivered to efferent fibers of the glossopharyngeal nerve independent of sensory or input signals detected or sensed regarding the neuromuscular state of the airway.

Regarding delivering an electrical neuromodulation signal to a target site comprising the ansa cervicalis in aspects referenced above, such delivery can activate one or more infrahyoid muscles and can include one or both of the superior root and the inferior root of the ansa cervicalis as well as proximate branches. Without wishing to be bound by theory, it is believed that activation of infrahyoid muscles (e.g. tightening of these muscles) can reduce upper airway compliance (e.g. stiffen the upper airway). Upper airway compliance can indicate the potential of the airway to collapse and can be relevant to treating SDB. Without wishing to be bound by theory, stimulation of the ansa cervicalis may anchor the inferior end of the pharynx by preventing upward movement of the thyroid cartilage and hyoid bone, which may allow contraction of the pharyngeal constrictor muscles and palatopharyngeus muscle to work against a solid anchor as opposed to a mobile insertion point, increasing the effectiveness of co-stimulation of the ansa cervicalis with stimulation of an efferent fiber of the glossopharyngeal nerve or stimulation of the palatopharyngeus muscle.

As explained below, the infrahyoid muscles include the sternohyoid muscle, the sternothyroid muscle, the omohyoid muscle, and the thyrohyoid muscle. In an embodiment, a method comprises delivering an electrical neuromodulation signal to a target site proximate to an ansa cervicalis that innervates at least the sternothyroid muscle to activate the sternothyroid muscle. A target site can be proximate to the ansa cervicalis such that delivering an electrical neuromodulation signal activates the motor fibers of the ansa cervicalis. It is believed that activation of at least the sternothyroid muscle can stiffen the patient's upper airway thereby improving a patient's SDB.

Figure 4:
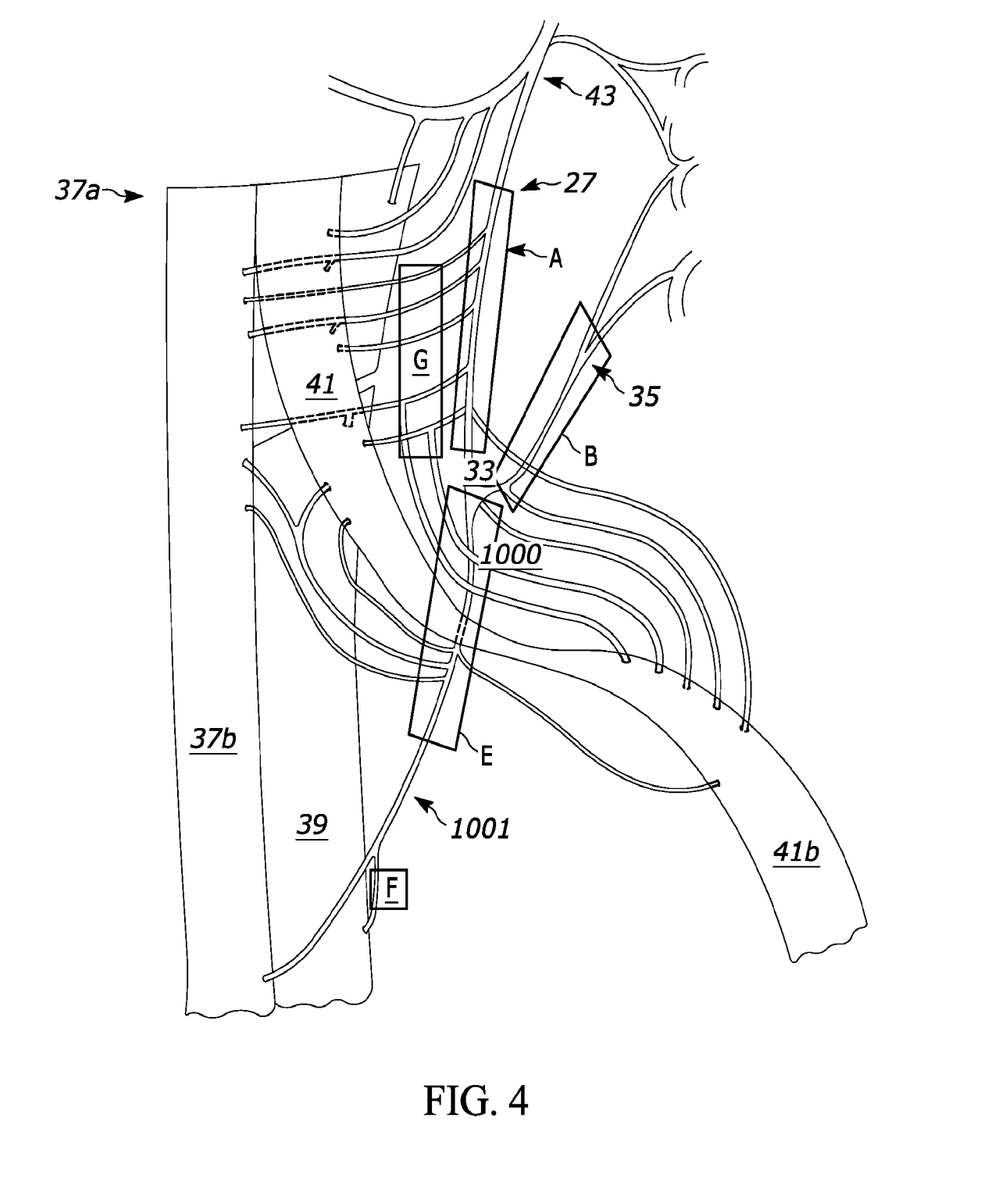
FIG. 4 is a schematic illustration of exemplary target sites for neuromodulation according to an aspect of the present disclosure.
Figure 5:
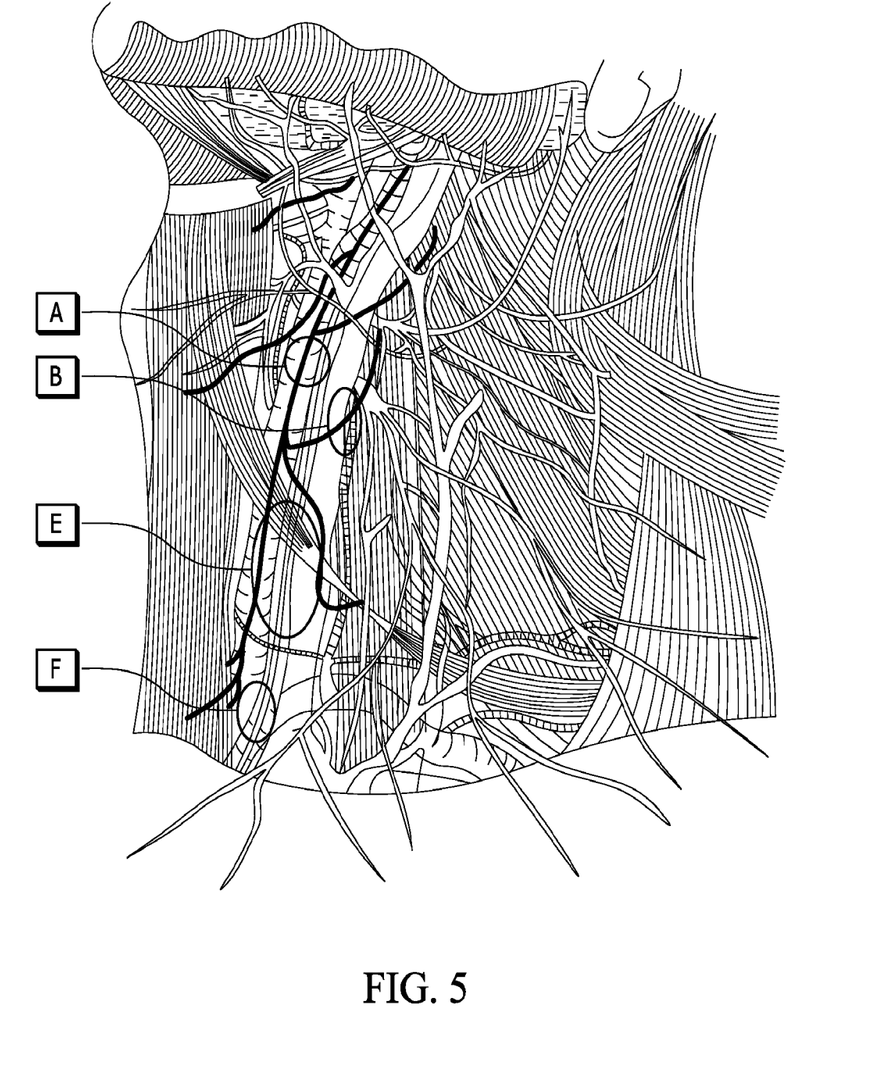
FIG. 5 is a schematic illustration of exemplary target sites for neuromodulation according to an aspect of the present disclosure.
Figure 6:
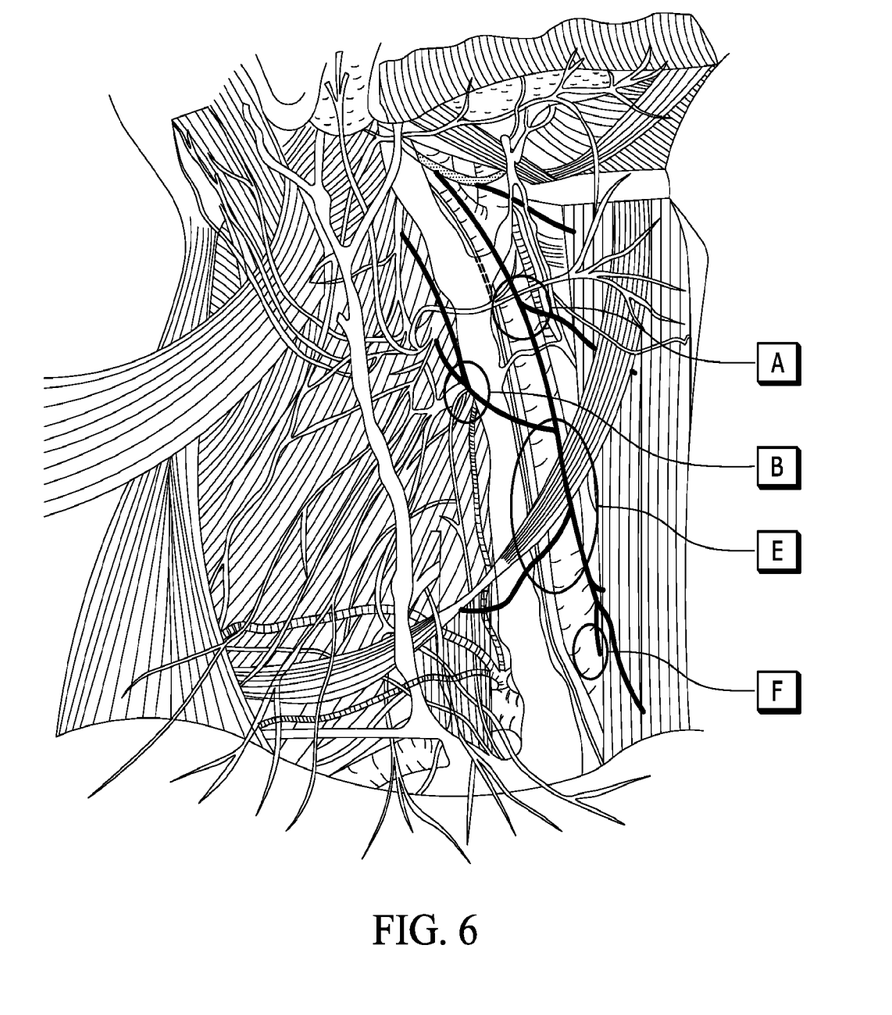
FIG. 6 is a schematic illustration of exemplary target sites for neuromodulation according to an aspect of the present disclosure

With reference to FIGS. 4-6, the infrahyoid strap muscles can be variably innervated by nerve fiber contributions from both the superior and inferior roots of the ansa cervicalis. Normal anatomic variants may necessitate use of one or more different target sites in different patients to achieve desired stimulation of the sternothyroid muscle 39. In certain aspects and with reference to FIG. 4, an electrical neuromodulation signal can be delivered to a target site proximate to the ansa cervicalis 33 that also innervates the superior belly of the sternohyoid muscle 37a or inferior belly of the sternohyoid muscle 37b to activate part of or all of the sternohyoid muscle 37. For example, an exemplary target site includes target site A, which can be proximal to or at the branch point 43 of the superior root of the ansa cervicalis 27 innervating the sternohyoid muscle 37 such that the sternohyoid muscle 37 is activated as well as the sternothyroid muscle 39. In certain aspects, delivering an electrical signal to target site A proximate to the superior root of the ansa cervicalis 27 can also activate part or all of the omohyoid muscle 41. If the target site were distal to the superior root of the ansa cervicalis 27 but not including branch point 1000 (e.g. placed in site G), an electrical neuromodulation signal may only activate the sternohyoid muscle 37 or omohyoid muscle 41 and not necessarily the sternothyroid muscle 39 along with the sternohyoid muscle 37 or omohyoid muscle 41. Without wishing to be bound by theory, it is believed that activation of at least the sternothyroid muscle 39, including the sternothyroid muscle 39, the sternohyoid muscle 37, and the omohyoid muscle 41 can stiffen the patient's upper airway thereby improving the patient's SDB.

In certain aspects, an electrical neuromodulation signal is delivered to target site B proximate the ansa cervicalis (e.g. proximate to the inferior root of the ansa cervicalis 35) also innervating the sternothyroid muscle 39 and sternohyoid muscle 37 and omohyoid muscle 41 to activate one or more of the innervated muscles. In certain aspects, an electrical neuromodulation signal can be delivered simultaneously to target sites A and B proximate the ansa cervicalis 31 in order to stimulate nerve branches from both the superior root 27 and inferior root 35 of the ansa cervicalis innervating the sternothyroid muscle 39 as well as the sternohyoid muscle 37 and omohyoid muscle 41. In certain aspects, delivering an electrical signal to target site E (e.g. proximate to or at the branch point of the common trunk nerve or nerves 1000 arising from the loop of the ansa cervicalis 33 combining nerve fibers from the superior root 27 and inferior root 35 and supplying at least the sternothyroid muscle 39 and variably the sternohyoid muscle 37 and omohyoid muscle 41) can activate at least the sternothyroid muscle 39 and in certain aspects, the sternohyoid muscle 37 and in certain aspects the omohyoid muscle 41. In certain aspects, delivering an electrical signal to target site F (e.g. proximate to or at the branch point of the sternothyroid muscle nerve or nerves from the common trunk 1001) can activate the sternothyroid muscle 39. It should be noted that the above target sites are only exemplary and an electrode or electrodes can be placed at other parts of the ansa cervicalis including branches thereof.

With respect to delivering an electrical neuromodulation signal to a target site comprising the HGN in aspects referenced above, such a target site can be proximate to the HGN that innervates the genioglossus muscle to activate the genioglossus muscle. A target site can be proximate to the HGN such that delivering an electrical neuromodulation signal activates the motor fibers of the HGN. Referring back to FIG. 4, in certain aspects, an electrical signal is not delivered to the HGN proximal to branch point 43 as it is believed that separate electrodes may be needed to potentially provide different strength or timing of stimulation to the ansa cervicalis and HGN. In other aspects, the HGN can be stimulated proximal or distal to the branch point of the retrusor muscle branches to the stylohyoid muscle or the hyoglossus muscle. Activation of the genioglossus muscle can cause the tongue to move forward and dilate/reinforce the patient's upper airway thereby improving a patient's SDB.

Figure 7:
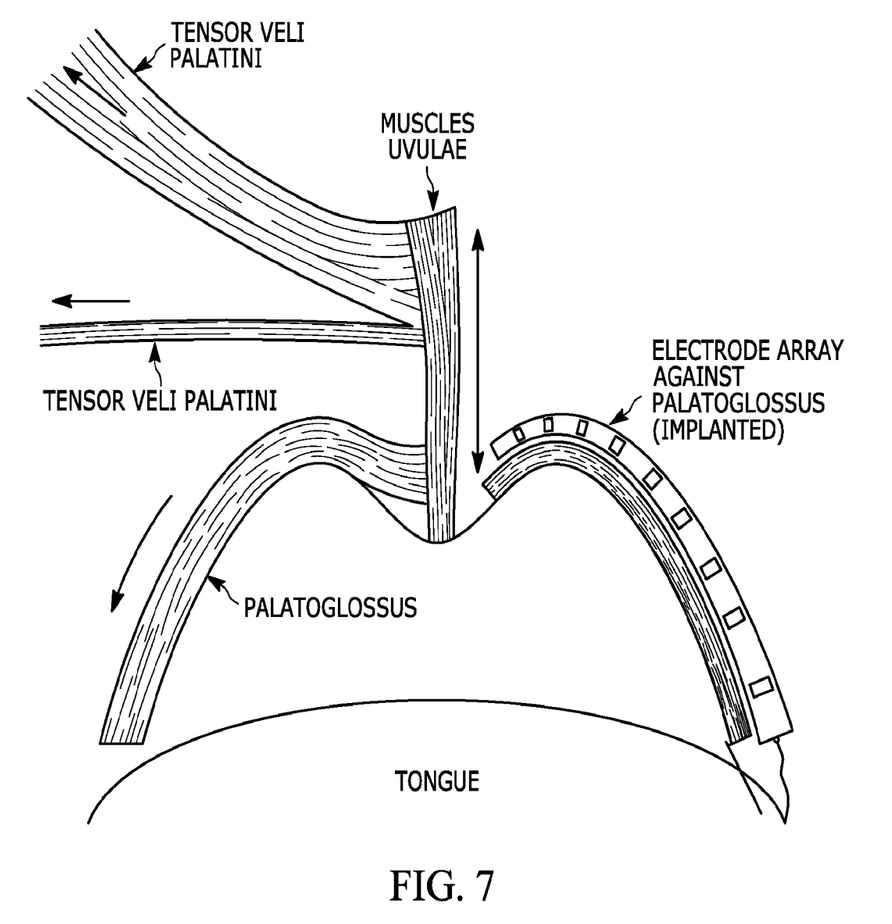
FIG. 7 is a schematic illustration of an electrode device placed against a palatoglossus muscle and also depicts other relevant surrounding anatomy.

With respect to delivering an electrical neuromodulation signal to a target site comprising the palatoglossus muscle or an innervating nerve fiber thereof in aspects referenced above, such delivery can cause anterior and inferior displacement of the soft palate, reducing collapse against the posterior pharyngeal wall and thereby dilating and opening the retropalatal airspace. The palatoglossus muscle originates from the palatine aponeurosis at the posterior part of the hard palate. It descends inferolaterally to insert into the posterolateral surface of the tongue. During its course through the posterior part of the oral cavity, it is covered medially by a mucous membrane, so forming the palatoglossus arch. The palatoglossus muscle functions to close off the oral cavity from the oropharynx by elevating the posterior tongue and drawing the soft palate inferiorly. This muscle is innervated by branches of the pharyngeal plexus, which is considered to function independently of the hypoglossal nerve and the rest of the intrinsic and extrinsic tongue musculature. Further with respect to relevant anatomy as schematically depicted in FIG. 7, the levator veli palatini functions to lift the soft palate into the nose (indicated by the arrow). If the soft palate is depressed, pulling the tensor veli palatini would elevate the soft palate. If the soft palate were elevated, pulling the tensor veli palatini would depress the soft palate. The tensor veli palatini functions to pulls the soft palate laterally (indicated by the arrow). This lateral movement stiffens the soft palate and returns it to a neutral plane. The musculus uvulae shortens the soft palate by pulling the uvula closer to the back edge of the hard palate (as indicated by the arrow). The palatoglossus muscle opposes the levator veli palatine, pulling the soft palate down towards the base of the tongue (as indicated by the arrow).

With respect to delivering an electrical neuromodulation signal to a target site comprising the palatopharyngeus muscle or an innervating nerve fiber thereof in aspects referenced above, the palatopharyngeus muscle primarily depresses the soft palate. It is innervated by branches of the pharyngeal plexus penetrating the overlying pharyngeal constrictor musculature. The muscle originates from the palatine aponeurosis. It descends inferolaterally to insert into the soft tissue of the pharyngeal wall. The palatopharyngeus muscle opposes the levator veli palatine. It can also cause the pharynx to elevate during contraction if it is not restricted from movement.

Aspects of the present disclosure also provide use of an electrode to deliver an electrical neuromodulation signal to a target site comprising an efferent fiber of the glossopharyngeal nerve that innervates one or more pharyngeal constrictor muscles or a stylopharyngeus muscle independent of a sensory or input signal detected or sensed regarding the neuromuscular state of the patient's airway to improve a patient's SDB. Aspects also include use of an electrode to deliver a first electrical neuromodulation signal to a target site comprising an efferent fiber of the glossopharyngeal nerve that innervates one or more pharyngeal constrictor muscles or a stylopharyngeus muscle and use of an electrode to deliver a second electrical neuromodulation signal to a target site comprising an ansa cervicalis that innervates one or more infrahyoid muscles to improve the patient's SDB.

Delivering an electrical neuromodulation signal can be accomplished by placing one or more electrodes/electrical contacts/neurostimulation devices proximate to a target site. The electrode can be placed proximate to a target site in a variety of different ways, such as, for example, transcutaneously, percutaneously, subcutaneously, intramuscularly, intraluminally, transvascularly, intravascularly, or via direct open surgical implantation. The electrode can also have different form factors such as, for example, an injectable microstimulator, a nerve cuff electrode, or a transcutaneous patch.

An electrode or neurostimulator can be placed on the same or different target sites. For example, if the target sites include two separate nerves or nerve segment, a separate nerve cuff electrode can be placed on each nerve or nerve segment with each nerve cuff electrode having its own cathode and anode but connected to the same pulse generator or separate nerve cuff electrodes connected to the same pulse generator but one nerve cuff electrode serving as the cathode and the other serving as the anode, where the electrical field generated captures both nerves or nerve segments. In certain embodiments, an electrode or electrodes configured to stimulate a nerve or nerve segment can be combined with an electrode configured to stimulate another nerve or nerve segment. Still alternatively, an electrode or electrodes configured to stimulate a nerve or nerve segment can be part of a device separate from a device configured to stimulate another nerve or nerve segment. The electrodes can be operably coupled to the same, single pulse generator or a separate pulse generator (either within the same physical housing or separate housings).

An electrode can be controllable to provide output signals that may be varied in voltage, frequency, pulse-width, current and intensity, for example. The electrode can also provide both positive and negative current flow from the electrode or can be capable of stopping current flow from the electrode or changing the direction of current flow from the electrode. An electrode can be in electrical communication with an electrical energy generator, such as a battery or pulse generator. For example, the electrical energy generator can include a battery that is rechargeable by inductive coupling. The electrical energy generator may be positioned in any suitable location, such as adjacent the electrode (e.g., implanted adjacent the electrode), or a remote site in or on the patient's body or away from the patient's body in a remote location. An electrode may be connected to the remotely positioned electrical energy generator wirelessly or via wires.

The electrical energy generator can control, for example, the pulse waveform, the signal pulse width, the signal pulse frequency, the signal pulse phase, the signal pulse polarity, the signal pulse amplitude, the signal pulse intensity, the signal pulse duration, and combinations thereof of an electrical neuromodulation signal. The electrical energy generator may be programmed to convey a variety of currents and voltages to one or more electrodes and thereby modulate the activity of a nerve, neuron, or nerve structure. The electrical energy generator may be programmed to control numerous electrodes independently or in various combinations as needed to provide neuromodulation. In some instances, an electrode may be powered by bringing a power source external to the patient's body into contact with the patient's skin, or which may include an integral power source.

An electrical neuromodulation signal may be constant, intermittent, varying or modulated with respect to the current, voltage, pulse-width, waveform, cycle, frequency, amplitude, and so forth. The waveform can be a sine wave, a square wave, or the like. The type of stimulation may vary and involve different waveforms. Optimal activation patterns may require a delay in one electrode before activating another or in another coordinated fashion to optimally open the airway, whether that involves simultaneous activation or staggered activation in a coordinated, adjustable fashion.

A controller or programmer may also be associated with the neurostimulation device. A programmer, for example, can include one or more microprocessors under the control of a suitable software program. The programmer can include other components such as an analog-to-digital converter, etc.

A neurostimulation device can be pre-programmed with desired stimulation parameters. Stimulation parameters can be controllable so that an electrical neuromodulation signal may be remotely modulated to desired settings without removal of the electrode from its target position. Remote control may be performed, e.g., using conventional telemetry with an electric signal generator and battery, a radiofrequency receiver coupled to an external transmitter, and the like.

Methods as disclosed herein can be used as part of a closed-loop system (as described in more detail below). Such a method can include sensing a physiological parameter associated with SDB, generating a sensor signal based on the physiological parameter, and activating the electrode to adjust application of the electrical signal to the target site in response to the sensor signal to improve the patient's SDB.

Figure 8:
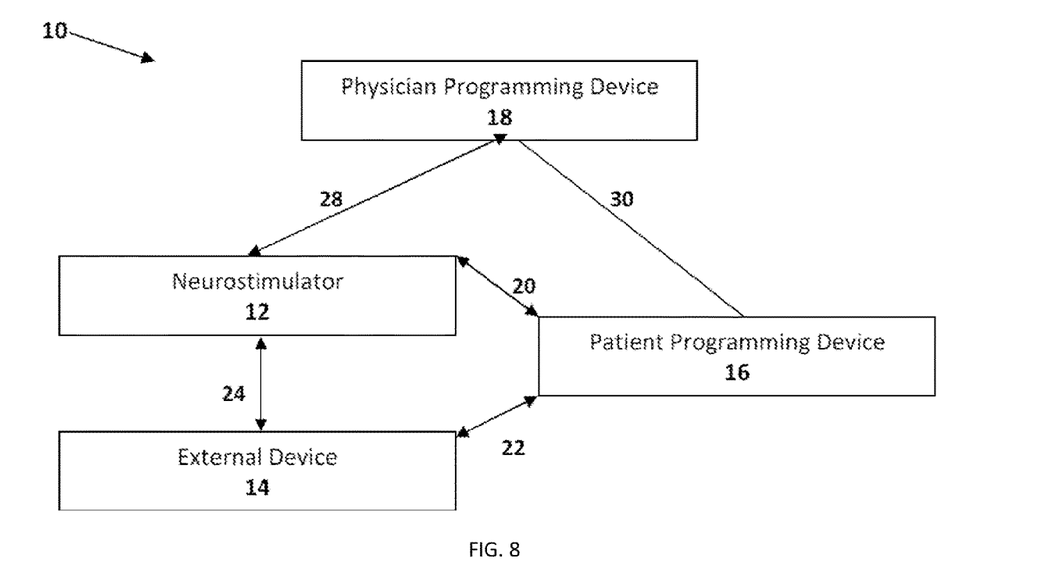
FIG. 8 is block diagram depicting illustrative components of a neuromuscular stimulation system according to an embodiment of the present disclosure.
Figure 9:
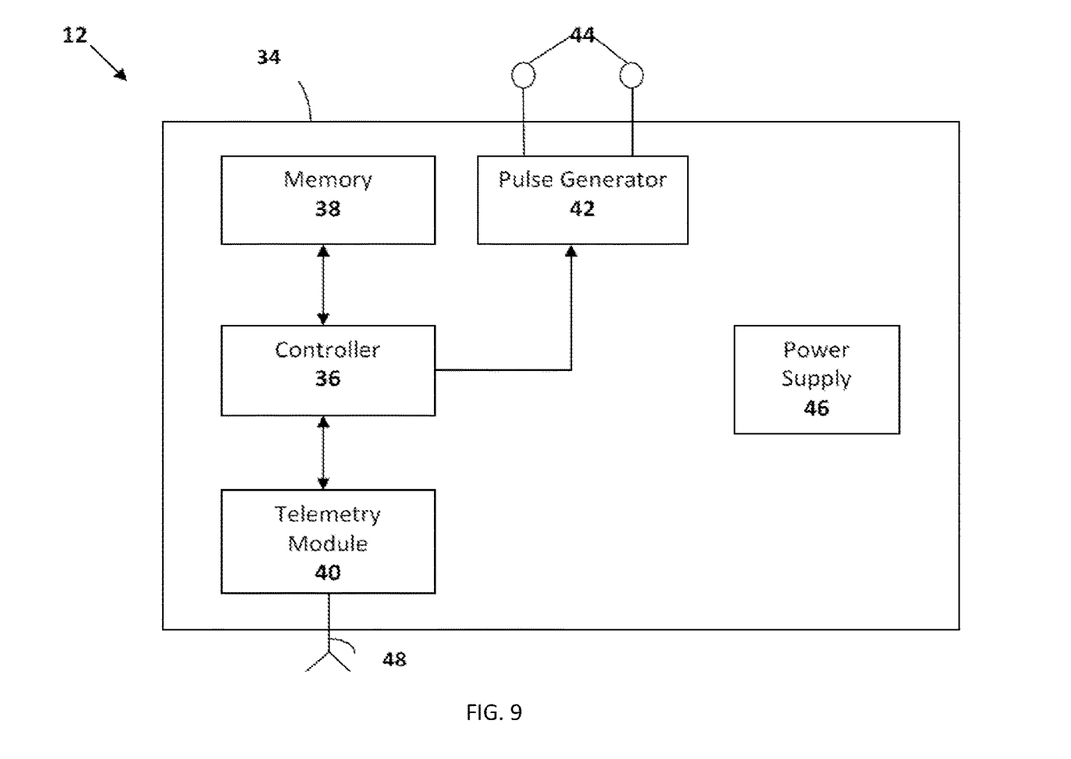
FIG. 9 is a block diagram depicting illustrative components of a neuromuscular stimulator according to an embodiment of the present disclosure.

Aspects of the present disclosure also provide systems for improving SDB in a patient suffering therefrom. With reference to FIGS. 8 and 9, in an embodiment, a neurostimulation system 10 includes a neurostimulator 12, an external device 14 that transmits signals to neurostimulator 12, a patient programming device 16 that bi-directionally communicates with neurostimulator 12 or an external device 14, and a physician programming device 18. As discussed below, each component of a system can be in communication (e.g., electrical communication) with one another. In some instances, two or more components of a system can be in wireless communication with one another. In other instances, two or more components of a system can be in wired communication with one another. As such, some components of a system can be in wireless communication with one another while other components are in wired communication with one another. Further, in the illustrative embodiments disclosed herein, communication between components included in neurostimulation system 10 is configured to be bidirectional in nature. However, communication between two or more system components can be unidirectional. Further, the functionality of different components of the system can be combined into a single device. For example, the functionality of components of the external device and the patient programming device can be combined into a single device.

In an embodiment, neurostimulator 12 includes electronic circuitry, such as one or more electronic circuits, for delivering neurostimulation pulses enclosed in a sealed housing and coupled to electrodes. In certain embodiments, neurostimulator 12 can include a primary battery cell, a rechargeable battery cell, or an inductively coupled power source for providing power for generating and delivering stimulation pulses and powering other device functions such as communication functions. Neurostimulator 12 or system 10 can include fixation members to secure the neurostimulator to tissue adjacent to the target site.

External device 14 can be a wearable device including a strap, patch or another attachment member(s) for securing external device 14 to the patient in operable proximity to neurostimulator 12. In some instances, external device 14 can be programmed to provide user feedback to assist the patient in optimizing placement of external device 14 about the subject's body. When neurostimulator 12 is provided with a rechargeable battery cell, external device 14 can include a recharging unit for transmitting power, for example inductive power transmission, from external device 14 to neurostimulator 12. In this embodiment, programming device 16 can be a patient handheld device that is used to initiate and terminate therapy delivered by neurostimulator 12 via a bidirectional wireless telemetry link 20. Alternatively, programming device 16 can be operated by a patient for communicating with wearable external device 14 to control therapy on and off times and other therapy control parameters, which are transmitted to neurostimulator 12 via communication link 24. Programming device 16 can communicate with wearable external device 14 via a bidirectional wireless telemetry link 22 that can establish communication over a distance of up to a few feet, enabling distance telemetry such that the patient need not position programming device 16 directly over neurostimulator 12 to control therapy on and off times or perform other interrogation or programming operations (e.g., programming of other therapy control parameters).

When neurostimulator 12 includes primary cell(s), external device 14 can be optional. Programming of neurostimulator 12 can be performed by programming device 16, using near- or distance-telemetry technology for establishing a bidirectional communication link 20 for transmitting data between programming device 16 and neurostimulator 12. Programming device 16 can be used by a patient or clinician to set a therapy protocol that is performed automatically by neurostimulator 12. Programming device 16 can be used to manually start and stop therapy, adjust therapy delivery parameters, and collect data from neurostimulator 12, e.g. data relating to total accumulated therapy delivery time or other data relating to device operation or measurements taken by neurostimulator 12. For example, programming device 16 can include software programmed to control one or more stimulation or control parameters associated with neurostimulator 12. Additionally, or optionally, the software comprising programming device 16 can be programmed to store patient therapy data, such as diary questions or physiologic measurements. Programming device 16 can also include software programmed to access remote data sources, query certain data, and then provide stimulation instructions to system 10 based on the queried data. For example, programming device 16 can include software programmed to provide neurostimulator 12 with customizable or patient-triggered alerts, e.g., indicating stimulation periods and the duration of each period, after a desired period of time (e.g., 30 minutes) after sleep onset. Programming device 16 can be embodied as a smart phone or tablet, although personal computers (PCs) may also be included.

When neurostimulator 12 is configured as an externally powered device, external device 14 can be a power transmission device that is worn by the patient during sleep to provide power needed to generate stimulation pulses. For example, external device 14 can be a battery-powered device including a primary coil used to inductively transmit power to a secondary coil included in neurostimulator 12. External device 14 can include one or more primary or rechargeable cells and therefore can include a power adaptor and plug for re-charging in a standard 110V or 220V wall outlet, for example.

In some embodiments, the functionality required for transmitting power to neurostimulator 12 when neurostimulator 12 is embodied as a rechargeable or externally powered device and for programming the neurostimulator 12 for controlling therapy delivery can be implemented in a single external device. For example, power transmission capability of external device 14 and programming capabilities of patient programmer 16 can be combined in a single external device, which can be a wearable or handheld device (such as, for example, a smart phone or tablet).

Physician programming device 18 can include increased programming and diagnostic functionality compared to patient programming device 16. For example, physician programming device 18 can be configured for programming all neurostimulation therapy control parameters, such as, but not limited to, pulse amplitude, pulse width, pulse shape, pulse frequency, duty cycle, therapy on and off times, electrode selection, and electrode polarity assignments. Patient programming device 16 can be limited to turning therapy on or off, adjusting a start time of therapy, or adjusting a pulse amplitude without giving the patient full access to full programming functions such that some programming functions and programmable therapy control parameters cannot be accessed or altered by a patient.

Physician programming device 18 can be configured to communicate directly with neurostimulator 12 via wireless, bidirectional telemetry link 28 for example during an office visit. Additionally or alternatively, physician programming device 18 can be operable as a remote programming instrument used to transmit programming commands to patient programming device 16 via a wired or wireless communication network link 30, after which patient programming device 16 automatically transmits programming data to neurostimulator 12 via bidirectional telemetry link 20 (or via wearable external device 14 and link 24). Physician programming device can be embodied as a smart phone, tablet or PC, for example.

In some embodiments, the patient can be provided with a magnet for adjusting operation of neurostimulator 12. For example, application of the magnet can turn therapy on or off or cause other binary or stepwise adjustments to neurostimulator 12 operations.

FIG. 9 is a functional block diagram of neurostimulator 12 of FIG. 8 according to an embodiment of a neurostimulation system. Neurostimulator 12 can include a housing 34 enclosing a controller 36 and associated memory 38, a telemetry module 40, and a pulse generator 42 coupled to electrode(s) 44. Neurostimulator 12 includes a power supply 46, which as described above can include any of a primary battery cell, a rechargeable battery cell, or a secondary coil of an externally powered system.

Controller 36 can include any one or more of a microprocessor, a digital signal processor (DSP), an application specific integrated circuit (ASIC), a field-programmable gate array (FPGA), or equivalent discrete or integrated logic circuitry. In some examples, controller 36 can include multiple components, such as any combination of one or more microprocessors, one or more controllers, one or more DSPs, one or more ASICs, or one or more FPGAs, as well as other discrete or integrated logic circuitry. The functions attributed to controller 36 herein can be embodied as software, firmware, hardware or any combination thereof. In one example, a neurostimulation therapy protocol to improve an SDB in a patient can be stored or encoded as instructions in memory 38 that are executed by controller 36 to cause pulse generator 42 to deliver the therapy via electrodes 44 according to the programmed protocol.

Memory 38 can include computer-readable instructions that, when executed by controller 36, cause neurostimulator 12 to perform various functions attributed throughout this disclosure to the neurostimulator. The computer-readable instructions can be encoded within memory 38. Memory 38 can comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory, propagating signal.

Telemetry module 40 and associated antenna 48 can be provided for establishing bidirectional communication with external device 14, patient programmer 16 or physician programmer 18. Examples of communication techniques used by neurostimulator 12 and programming device 16 or 18 include low frequency or radiofrequency (RF) telemetry, which can be an RF link established via Bluetooth, WiFi, or MICS, for example. Antenna 48 can be located within, along or extend externally from housing 34.

Electrodes 44 can be located along an exterior surface of housing 44 and can be coupled to pulse generator 42 via insulated feedthroughs or other connections as will be further described below. In other embodiments, electrodes 44 can be carried by a lead or insulated tether electrically coupled to pulse generator 42 via appropriate insulated feedthroughs or other electrical connections crossing sealed housing 34. In still other embodiments, electrodes 44 can be incorporated in housing 34 with externally exposed surfaces adapted to be operably positioned in proximity to a target site proximate to a nerve and electrically coupled to pulse generator 42.

In another aspect, system 10 can include one or more sensors (not shown) to permit open- or closed-loop control. In an open-loop system, for example, system 10 can include one or more sensors such that a patient can manage (e.g., prophylactically) improvement of the SDB based on feedback (e.g., detected signals) from the sensor(s). Such detected signals can be indicative of the onset of the SDB, such as changes in muscle or nerve electrical activity, tongue position, oropharyngeal airflow, etc. Upon noticing the signal(s), the patient can then trigger or activate the neurostimulator 12 to prevent or mitigate the SDB.

In another aspect, system 10 can include one or more sensors to permit closed-loop control by, for example, automatically responding (e.g., by activation of the neurostimulator 12) in response to a sensed physiological parameter, or a related symptom or sign, indicative of the extent or presence of the SDB. Physiological parameters include changes in muscle or nerve electrical activity, tongue position, changes in heart rate or blood pressure, pressure changes in response to respiratory effort, oropharyngeal airflow, etc. Sensors used as part of a closed- or open-loop system can be placed at any appropriate anatomical location on a patient, including a skin surface, an oral cavity, a nasal cavity, a mucosal surface, or at a subcutaneous location.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance. Further, while the above is described with respect to electrical stimulation, other forms of energy could be used, such as, for example, ultrasound, magnetic, or optical energy.

What is claimed is:

1. A method to improve obstructive sleep apnea comprising:
placing one or more electrodes on an efferent fiber nerve branch and not a sensory fiber of the glossopharyngeal nerve that innervates one or more pharyngeal constrictor muscles and a stylopharyngeus muscle;
and delivering one or more electrical neuromodulation signals to the efferent fiber nerve branch to activate the one or more pharyngeal constrictor muscles and the stylopharyngeus muscle;
improving the obstructive sleep apnea.

2. The method of claim 1, further comprising delivering an electrical neuromodulation signal to a target site comprising an ansa cervicalis that innervates one or more infrahyoid muscles.

3. The method of claim 2, wherein the delivering steps occur at a pre-determined time period or a series of pre-determined time periods.

4. The method of claim 2, wherein the delivering steps occur at substantially a same time period.

5. The method of claim 2, wherein delivering the electrical neuromodulation signal to the target site comprising the ansa cervicalis that innervates one or more infrahyoid muscles comprises delivering the electrical neuromodulation signal to the target site innervating the sternothyroid muscle.

6. The method of claim 2, wherein delivering the electrical neuromodulation signal to the target site comprising the ansa cervicalis that innervates one or more infrahyoid muscles comprises delivering the electrical neuromodulation signal proximal to or at a branch point of a superior root of the ansa cervicalis.

7. The method of claim 2, wherein delivering the electrical neuromodulation signal to the target site comprising the ansa cervicalis that innervates one or more infrahyoid muscles comprises delivering the electrical neuromodulation signal proximate to the inferior root of the ansa cervicalis.

8. The method of claim 2, wherein delivering the electrical neuromodulation signal to the target site comprising the ansa cervicalis that innervates one or more infrahyoid muscles comprises delivering the electrical neuromodulation signal to the target site innervating the omohyoid muscle.

9. The method of claim 1, further comprising delivering an electrical neuromodulation signal to a target site comprising a hypoglossal nerve (HGN).

10. The method of claim 9, wherein delivering the electrical neuromodulation signal to the target site comprising the HGN comprises delivering the electrical neuromodulation signal to the target site comprising the HGN that innervates at least the genioglossus muscle.

11. The method of claim 9, wherein the target site comprising the HGN is distal to or at a branch point of the HGN and a superior root of an ansa cervicalis.

12. The method of claim 9, wherein the target site comprising the HGN is distal to a branch point of the HGN innervating tongue retractor muscles.

13. The method of claim 1, further comprising delivering an electrical neuromodulation signal to a palatoglossus muscle, a palatopharyngeus muscle, a nerve fiber innervating the palatoglossus muscle, or a nerve fiber innervating the palatopharyngeus muscle.

14. The method of claim 1, wherein delivering the electrical neuromodulation signal to the efferent fiber of the glossopharyngeal nerve comprises delivering the electrical neuromodulation signal to the pharyngeal plexus.

* * * * *